US010209265B2

(12) United States Patent
Sample et al.

(10) Patent No.: US 10,209,265 B2
(45) Date of Patent: Feb. 19, 2019

(54) CHAIN OF CUSTODY FORMS AND METHODS

(75) Inventors: R. H. Barry Sample, Seneca, SC (US); Eric Quilter, Park City, UT (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 12/339,287

(22) Filed: Dec. 19, 2008

(65) Prior Publication Data

US 2009/0289448 A1    Nov. 26, 2009

Related U.S. Application Data

(63) Continuation of application No. 12/106,478, filed on Apr. 21, 2008, now abandoned.
(Continued)

(51) Int. Cl.
| | | |
|---|---|---|
| *B42D 15/00* | (2006.01) | |
| *B42D 15/10* | (2006.01) | |
| *G09C 3/00* | (2006.01) | |
| *G01N 35/00* | (2006.01) | |
| *B01L 3/00* | (2006.01) | |
| *G09F 3/00* | (2006.01) | |
| *G09F 3/03* | (2006.01) | |
| *B42D 5/00* | (2006.01) | |

(52) U.S. Cl.
CPC ...... *G01N 35/00722* (2013.01); *B01L 3/5457* (2013.01); *B42D 15/00* (2013.01); *G09F 3/0288* (2013.01); *G09F 3/03* (2013.01); *G09F 3/0341* (2013.01); *B01L 2200/141* (2013.01); *B42D 5/002* (2013.01); *B42D 2035/08* (2013.01); *B42D 2035/16* (2013.01); *G01N 35/00613* (2013.01); *G01N 35/00732* (2013.01)

(58) Field of Classification Search
CPC ............... B42D 15/00; B42D 2035/08; B42D 2035/16; B42D 5/002; G01N 35/00722; G01N 35/00732; G01N 35/00613; B01L 3/5457; B01L 2200/141; G09F 3/0288; G09F 3/0341; G09F 3/03
USPC ........ 281/51; 283/55, 61, 62, 67, 70, 72, 74, 283/81, 117, 900; 340/10.1, 540, 572.1, 340/573.1
See application file for complete search history.

(56) References Cited

U.S. PATENT DOCUMENTS 5,050,909 A * 9/1991 Mertens et al. ................. 283/81
6,158,779 A * 12/2000 Petrick ........................... 283/81
(Continued)

*Primary Examiner* — Justin V Lewis
(74) *Attorney, Agent, or Firm* — Jon E. Gordon; Haug Partners LLP

(57) ABSTRACT

A chain-of-custody form has integrated removable specimen seals, and the form may be used to identify a test sample collected from a donor and to document the handling of the test sample. The form may be printed upon a single sheet that has a first portion and a second portion. The first portion includes a first section having one or more spaces for recording demographic and testing information, and one or more indicia of the information to be recorded in one or more marked spaces; and a second section having a marked space for the donor to affix a signature and one or more indicia of the purpose of the space. An identifier that is unique to the form is recorded within the first portion and within the second portion. The identifier includes an specimen identification number or some other method of specimen identification such as a bar-code.

15 Claims, 7 Drawing Sheets

Related U.S. Application Data

(60) Provisional application No. 60/912,926, filed on Apr. 19, 2007.

(56) References Cited

U.S. PATENT DOCUMENTS

| | | | |
|---|---|---|---|
| 6,196,593 B1 * | 3/2001 | Petrick et al. | 283/81 |
| 6,343,695 B1 * | 2/2002 | Petrick et al. | 283/81 |
| 6,535,129 B1 * | 3/2003 | Petrick | G06K 17/0022 |
| | | | 283/75 |
| 2004/0164545 A1 * | 8/2004 | Christianson et al. | 283/81 |

* cited by examiner

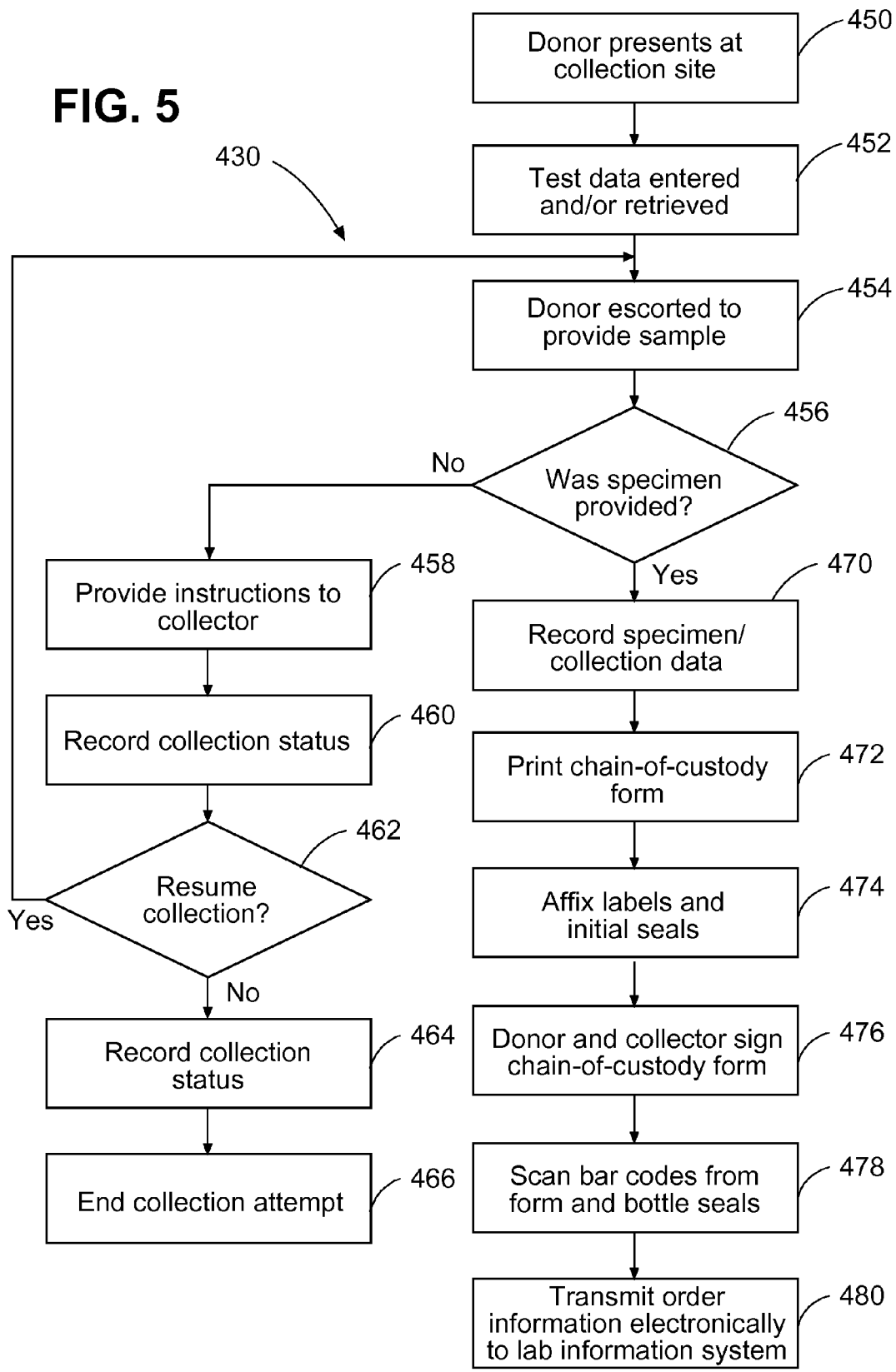

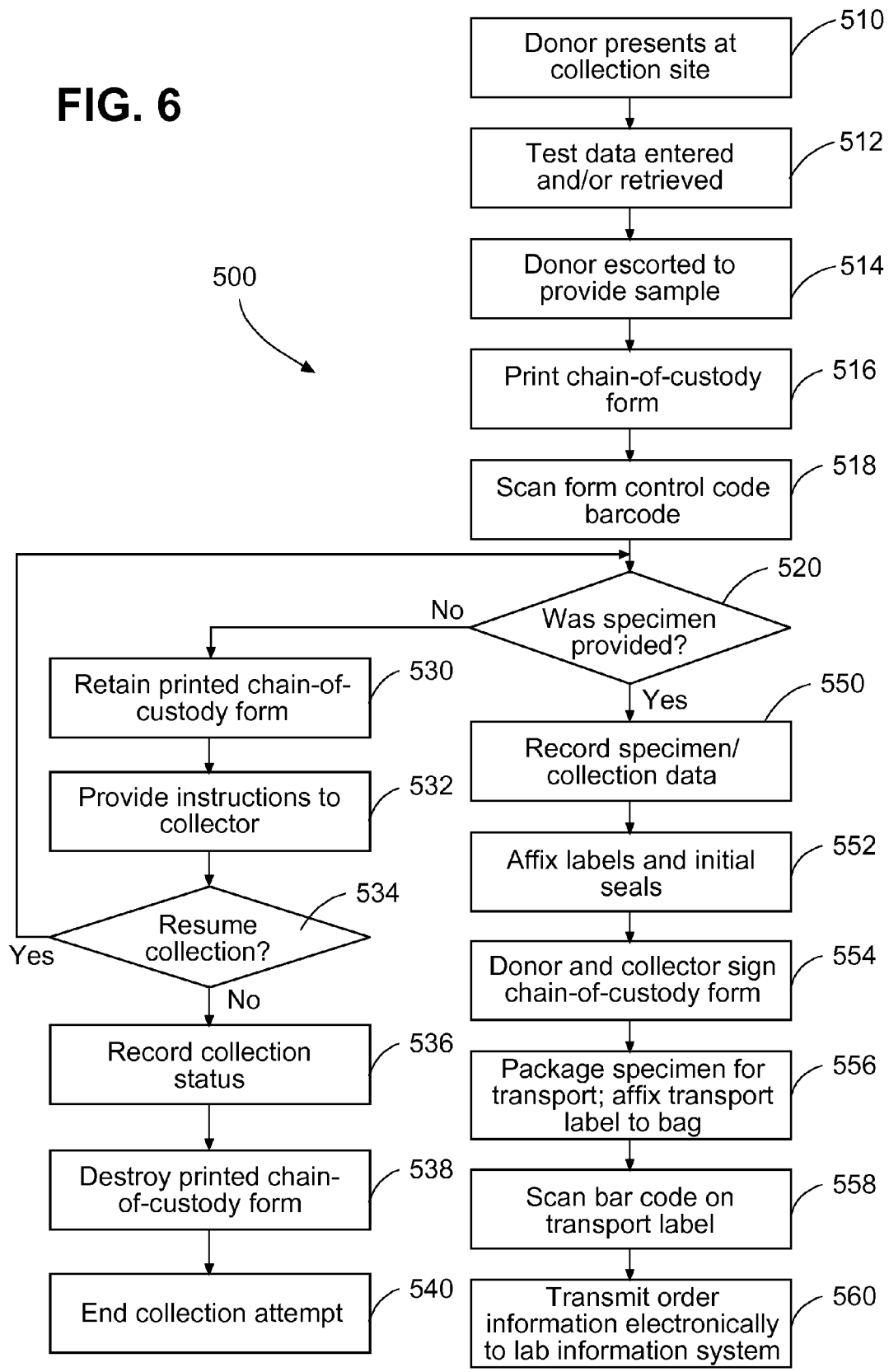

CHAIN OF CUSTODY FORMS AND METHODS

CROSS-REFERENCE TO RELATED APPLICATION

This application is a continuation of U.S. patent application Ser. No. 12/106,478, filed Apr. 21, 2008, now abandoned and entitled "CHAIN OF CUSTODY FORMS AND METHODS."

COPYRIGHT NOTICE

A portion of the disclosure of this patent document contains material that is subject to copyright protection. The copyright owner has no objection to the facsimile reproduction by anyone of the patent document or the patent disclosure, as it appears in the patent files or records of the U.S. Patent and Trademark Office, but otherwise reserves all copyrights whatsoever.

BACKGROUND

The present invention relates to forms and methods of using forms to record a chain of custody. More specifically, it relates to a composite form, e.g., one that is printed upon a single sheet, comprising removable seals that are integrated into the form. The invention also relates to methods of using such a form to record the handling of a specimen from the time of collection until arrival at the laboratory, thereby ensuring both the integrity of the specimen and the accountability of those who handle it.

The term "chain of custody" often refers to documenting the acquisition, handling, transfer, and/or disposition of an object or information. A chain of custody may be maintained, e.g., when an object needs to be protected from tampering. For example, a chain of custody may record the handling of a handgun found at a crime scene, from the finding of gun to the final disposition of any criminal charges. By identifying everyone who handled the gun, the chain of custody permits proof at trial that no one tampered with it, e.g., by altering fingerprints or damaging DNA that may be evidence of guilt. A chain of custody commonly includes both positively identifying everyone who handles the evidence and preventing unrecorded handling, and may include records relating to the conditions under which the evidence has been handled, e.g., transported and/or stored.

In the field of laboratory analysis of biological samples, maintaining a chain of custody often refers to documenting the identity and handling of a specimen from the time it is collected until it is delivered to the laboratory and, possibly, even to an analyst or technician within the laboratory. Proper maintenance of the chain of custody protects the integrity of testing by identifying anyone who might have an opportunity to tamper with a test sample and preventing tests on specimens that may have suffered contamination consequent to tampering by persons not responsible for collection, processing, or analysis of the samples. Ensuring the integrity of the process may be desirable, e.g., when the test results may have serious legal and/or economic consequences, such as when the specimen is a urine, blood, oral fluid (e.g., saliva), sweat, or hair sample that is to be tested for evidence of the donor's drug use.

Maintaining a chain of custody often involves requiring each individual involved in each transfer of the samples to record the time and date of transfer on a signed chain of custody form. The form thereby documents the transfer of the specimen from the collector or other test administrator, often through another person, such as a courier, to the analyst at the laboratory. The process often includes strict security procedures to prevent tampering or contamination. For example, a container is typically sealed with a tamper-evident adhesive seal immediately after collection. If an analyst or other representative at the laboratory determines from the apparent condition of the seal that it has been tampered with, the sample will not be tested.

According to the prior art, the chain of custody is recorded on documents that create multiple identical sheets using carbon or carbonless paper, which are typically filled out by hand. The multiple sheets are commonly used to provide a record of the collection event to some or all parties involved in collection and testing, e.g., the collector, the employer or other requesting authority, the donor, the laboratory, and/or the Medical Review Officer) Conventional label printers may also generate sheets of specimen seals that include identification codes in human-readable (e.g., printed alphanumeric characters) and/or machine-readable (e.g., bar code) formats.

SUMMARY

An embodiment of the invention includes a composite blank form for identifying a test sample collected from a donor and documenting the handling of the sample. According to an embodiment of the invention, the blank form comprises a sheet, e.g. of paper, that includes at least a first portion and a second portion. The first portion comprises a first section having one or more spaces for recording demographic and test information, and one or more indicia of the information to be recorded in one or more marked spaces; and a second section within the first portion, having a marked space for the donor to affix a signature and one or more indicia of the purpose of the space. Each portion includes an identifier that is unique to the form.

In some embodiments of the invention, the form comprises only a single page. In other embodiments of the invention, the form comprises more than one page, and the pages have been joined in a tamper-evident fashion. For example, the form may comprise a single sheet folded into two or more pages or joined in some other way such that tampering with the form (e.g., separating one or more pages) is evident.

Thus, in an embodiment of the invention, a form is provided for identifying a test sample collected from a donor and documenting the handling of the test sample. The form comprises a single printable sheet that comprises at least a first portion and a second portion. The first portion in turn comprises a first section comprising one or more spaces for recording demographic and test information and one or more indicia of the information to be recorded in one or more marked spaces and a second section comprising a marked space for the donor to affix a signature and one or more indicia of the purpose of the space. The second portion comprises at least one seal.

In an embodiment of the invention, the sheet comprises a perforation for separating the second portion from the first portion.

In an embodiment of the invention, the sheet comprises an identifier that is unique to the form and is recorded at least once within the first portion and at least once upon each seal in the second portion. In an embodiment of the invention, the identifier comprises a form control code that is unique to the blank form. In some such embodiments of the invention, the identifier is present in human-readable form, and in some such embodiments of the invention, the identifier is present in machine-readable form. According to a further embodiment of the invention, the printable sheet comprises a third portion, which may serve as a donor receipt, and the identifier is recorded at least once within the third portion.

In an embodiment of the invention, the sheet comprises a third portion; a perforation for separating the first portion from the second portion or the third portion; and a perforation for separating the second portion from the first portion or the third portion. In such an embodiment of the invention, the form may comprise an identifier that is unique to the form, and the identifier is recorded, in human-readable form and/or machine-readable form, at least once within the first portion, the third portion, and each seal within the second portion.

According to an embodiment of the invention, a method is provided for recording the handling of a specimen sample. The method comprises providing a form that comprises data and a first computer that is capable of recording data and printing to a printer. The method further comprises recording demographic and test data that corresponds to at least some of the data comprised by the form and printing, through the printer, the form upon a single printable sheet.

In an embodiment of the invention, the sheet comprises an identifier unique to the sheet and further comprises a first portion and a second portion, such that the identifier is recorded at least once within the first portion, at least some of the recorded demographic and test data is printed upon the first portion, the second portion comprises at least one specimen seal, and the identifier is recorded at least once within each seal.

In an embodiment of the invention, the method further comprises collecting, under the supervision of a test administrator, at least one specimen from a donor in at least one specimen container, each specimen container containing material from at most one specimen; closing each specimen container; separating at least one specimen seal from the second portion and affixing each separated specimen seal to a specimen container so that the specimen container cannot be opened without either removing the specimen seal or visibly damaging the specimen seal; affixing a signature of the administrator to the first portion, transferring the form and the at least one specimen to a laboratory; and affixing a signature of an accessioner within the laboratory to the form upon receipt of the specimen at the laboratory.

BRIEF DESCRIPTION OF THE DRAWINGS

The accompanying drawings depict certain embodiments of the invention and form a part of the disclosure of this invention. While the written and illustrated disclosure herein amplifies example embodiments of the invention, they are by way of illustration and example only, and the invention is not limited thereto. The spirit and scope of the present invention are limited only by the terms of the appended claims.

FIG. 5 depicts collection of a sample as may take place in connection with embodiments of the invention.

FIG. 6 depicts alternative collection of a sample as may take place in connection with embodiments of the invention.

DETAILED DESCRIPTION

The following description is provided to enable any person skilled in the art to make and use the invention and is provided in the context of a particular application. Various modifications to the described embodiments are possible, and the generic principles defined herein may be applied to these and other embodiments and applications without departing from the spirit and scope of the invention. Thus, the invention is not limited to the embodiments and applications shown, but is to be accorded the widest scope consistent with the principles, features, and teachings disclosed herein.

Figure 1A:
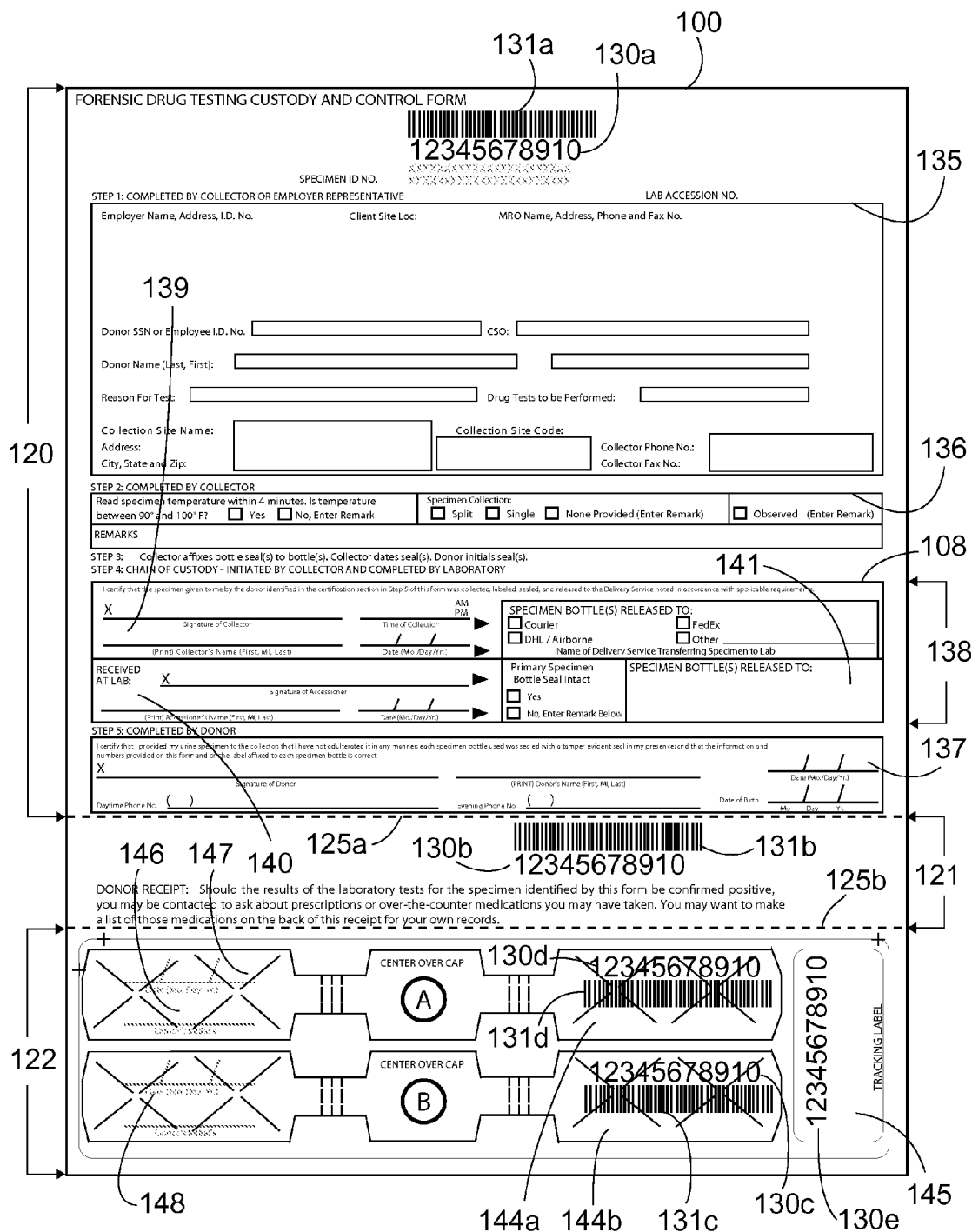
FIG. 1A depicts a blank chain-of-custody form according to an embodiment of the invention.
Figure 1B:
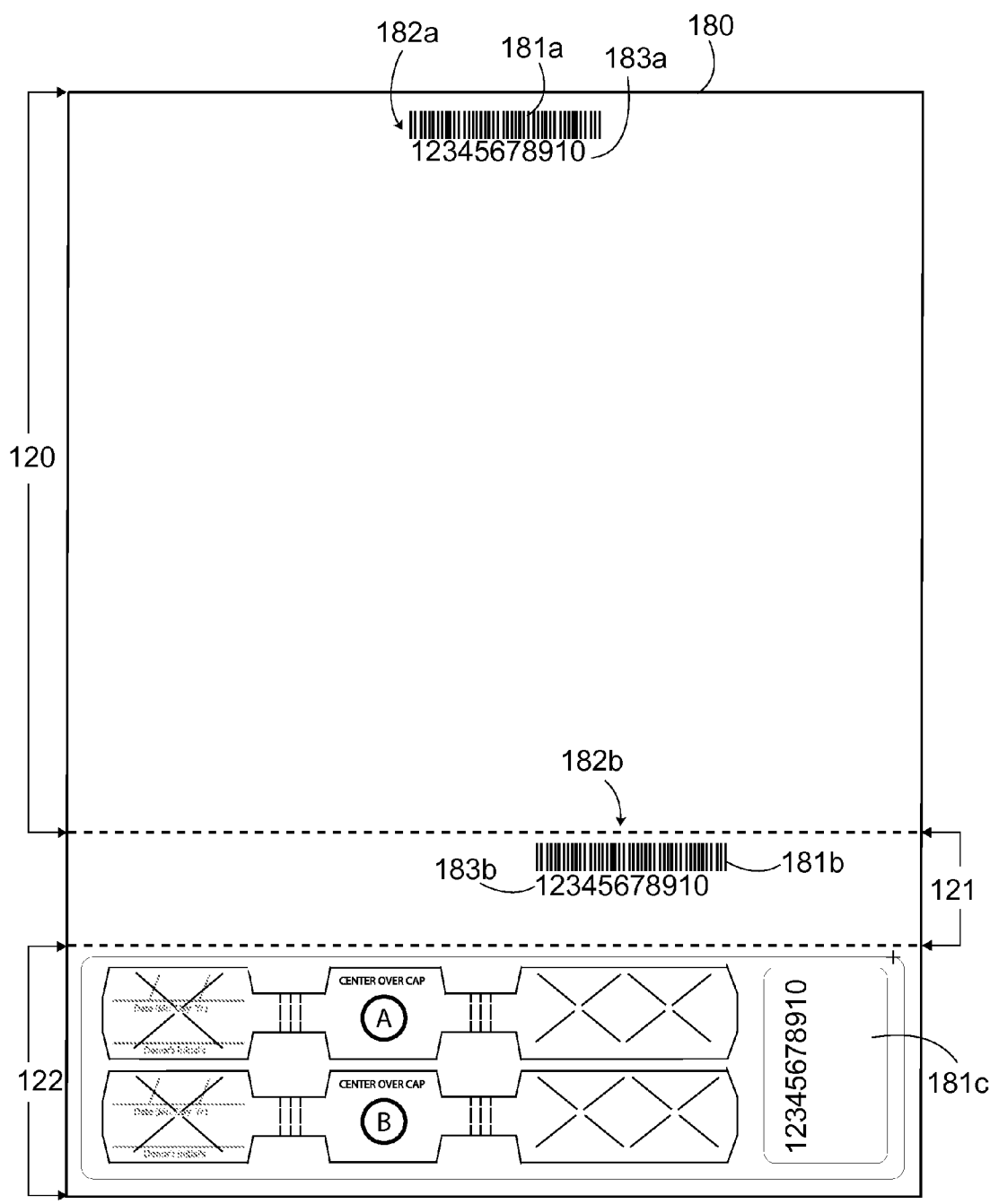
FIG. 1B depicts a blank chain-of-custody form according to an embodiment of the invention.

Embodiments of the invention may comprise a blank form implemented upon a single printable sheet. FIGS. 1A and 1B depict such a blank form 100, which may be used to maintain a chain of custody for a laboratory specimen according to an embodiment of the invention. In one embodiment of the invention, the blank form 100 is a printed form made from paper, card stock, and/or any other substance that may be used with any printing technology that may be used in connection with an electronic computer. Some or all of the blank form may be backed with an adhesive, e.g., a pressure-sensitive adhesive with a removable backing.

The blank form 100 is preferably printed, e.g., during manufacture or at the time of use, on white (or other light color) stock to provide a uniform background for visible printing. The blank form 100 may be provided in any convenient size, such as, e.g., A4 or 8½ inches by 11 inches.

As depicted in FIG. 1A, the blank form 100 comprises a data portion 120, a receipt portion 121, and a seal portion 122. In an embodiment of the invention, the blank form 100 may be perforated and/or scored 125 to ease separation of one portion from another. Instead of or in addition to the perforation or scoring, the blank form 100 may include visual indicia, e.g., a dashed line, indicating a place or places where the blank form 100 is to be cut to separate one portion from another.

In an embodiment of the invention, the blank form 100 includes an identifier, which may be referred to herein as a "form control code", which appears at least once in each portion and comprises information sufficient to function as an identifier. The form control code preferably consists of one or more sequences of digits or, alternatively, of alphanumeric characters and is globally unique to the blank form 100 on which it appears. In a preferred embodiment of the invention, at least a human-readable representation 130 of the form control code is present within each portion of the blank form 100. In some embodiments of the invention, a machine-readable representation 131 (e.g., a bar code) of the form control code may accompany or take the place of the human-readable representation.

In a preferred embodiment of the invention, the form control code 130 is printed on each blank form 100 as the blank form 100 is manufactured, in conjunction with a process that ensures that no two blank forms 100 share a form control code 130. In an alternative embodiment of the invention, the form control code 130 may be applied to the form after manufacture thereof, e.g., at the time that the form is put into use. In such an embodiment, the form control code may be, e.g., handwritten, typed, or stamped on the blank form 100 or printed on it when the blank form passes through a printer.

Aside from the form control code 130a, the data portion 120 includes several sections that each comprise one or more marked spaces for recording information and one or more indicia of the information to be recorded in each of the respective marked spaces. In a preferred embodiment of the invention, some or all requested information is obtained through one or more computer software applications, and the obtained information is inserted, e.g., by passing the blank form 100 through a printer. In addition to or instead of the foregoing, some or all of the information may be otherwise entered, e.g., by handwriting, typing, and/or inked stamps.

A requisition data section 135 in the data portion 120 comprises one or more marked spaces for recording demographic and test data and one or more indicia of the data to be recorded in the one or more marked spaces. As depicted in FIG. 1A, the requisition data section 135 includes spaces for the following data: the name, address, and identification number (if applicable) of the donor's employer; the name and address of a Medical Review Officer ("MRO"); the name, social security number, and/or other identifying information of the donor; the type of specimen collected (e.g., urine, saliva, hair, or blood), the reason for the test, the test to be performed, the collection site address, and phone and fax numbers of the person who collected the sample from the donor.

The data portion 120 also includes a collection data section 136, which, in connection with an embodiment of the invention, is completed and signed by collection site personnel. In an embodiment of the invention, the collection data section 136 records data related to the procedure and circumstances under which the specimen was obtained. As depicted in FIG. 1A, the collection data section 136 includes spaces to record data that includes, for example, whether the specimen was within a specified range of temperatures at the time of receipt, whether the specimen collected was split or single, whether the collection was observed, and any remarks that may be pertinent.

In an embodiment of the invention, the data portion 120 includes a donor certification section 137. As depicted in FIG. 1A, the donor certification section 137 includes spaces for the donor's printed name and signature, telephone numbers, and date of signature. This section also includes a statement to the effect that, by signing in the indicating space, the donor certifies that the donor gave the specimen to the collector, that the donor has not tampered with the specimen, and that the data on the form and specimen bottles is correct. ("Collector" is used in a broad sense herein and, as with "administrator," may refer to, e.g., a person or persons administering the test and/or supervising acquisition of the specimen from the donor.) The donor's signature also acknowledges that each specimen container was sealed, in the donor's presence, with a tamper-resistant seal.

In an embodiment of the invention, the data portion 120 includes a chain-of-custody section 138. As depicted in FIG. 1A, the chain-of-custody section 137 includes a collector's certification area 139, containing spaces for the collector's printed name and signature, the date and time of collection, and the identity of the delivery service—which may be, e.g., a common carrier, such as DHL or FedEx, or a courier—that is to carry the specimen to the laboratory for analysis.

As depicted in FIG. 1A, the chain-of-custody section 138 also includes a recipient's signature area 140. In this area, the person receiving the specimen from the delivery service (the "Accessioner") may enter a signature, printed name, and date, along with a space for indicating whether the specimen's seals were intact on receipt.

The blank form 100 depicted in FIG. 1A is used in connection with a laboratory that maintains a separate chain of custody once a specimen has been received at the testing facility. Thus, the recipient's signature area 140 includes a space 141 only for the name of the person within the facility to whom the specimen or specimens were released. In connection with another embodiment of the invention, the laboratory may use a single form to record both external and internal chain of custody, and the blank form in such cases (not pictured) may include additional area for recording the handling of the specimen or specimens within the facility.

In an embodiment of the invention, the form 100 may include a receipt portion 121 that comprises the unique form control code 130b. In an embodiment of the invention, the receipt portion is detached from the data portion 120 after collection of the specimen and signature of the designated sections of the data portion. The detached receipt portion 121 is provided to the donor after the specimen is collected and the required sections of the form 100 have been completed and signed.

Depending on the embodiment of the invention, the receipt portion 121 may include other information. Such other information may include, for example, contact information, including telephone numbers, facsimile numbers and e-mail addresses, for the laboratory responsible for performing the analyses. The donor receipt may also include instructions from the laboratory to the donor, e.g., as depicted in FIG. 1, suggesting that the donor record information on the receipt portion 121 about currently taken medications in case the test should find questionable substances in the sample.

According to embodiments of the invention, the seal portion 122 of the form 100 includes one or more generally elongated security seals 144 and one or more generally rectangular tracking labels 145. As depicted in FIG. 1A, each seal 144 includes the form control code 130, as does the tracking label 145. In the depicted embodiment of the invention, each seal 144 includes a marked space for the donor's initials 146 and another for the date 147, each adjacent to markings indicating the purpose of the respective spaces.

In an embodiment of the invention, both seals 144 and the tracking label 145 are backed by a pressure sensitive adhesive such as is well known in the art. The perimeters of each are preferably die cut to permit the seals 144 and the tracking label 145 to be readily separated by hand from the blank form 100. In the depicted embodiment of the invention, each seal 144 is scored 148 several times in an "X" pattern, which is intended to improve the tamper-resistance of each seal 144 by drastically increasing the difficulty of removing a seal 144 intact from a specimen container.

The color, size, printing, and configuration of the seals 144 and tracking label 145 may vary substantially from the depiction in FIG. 1A. In any particular embodiment of the invention, the shape and size of the seal or seals may be determined based on the space available on the sheet used to create each blank form 100 and the intended function of a seal. That is, once a seal has been applied to a closed container, an attempt to tamper with the container's contents is intended to result in a conspicuous and irreversible change to the seal.

For example, the seals 144 depicted in FIG. 1A may be used, among other possibilities, with a container, possibly for a liquid specimen, that has a circular, screw-top or flip-top lid. With the seal 144 centered on the lid, the sides extend over the edge and down opposite sides of the container. So configured, any attempt to open the lid may be expected to break the seal 144, particularly along a scored portion 148. In connection with another embodiment of the invention, one or more seals may take different shapes. For example, a rectangular seal (not pictured) may provide a tamper-evident seal on a container designed for hair or sweat specimens.

The rectangular tracking label 145 may, in connection with an embodiment of the invention, be secured, e.g., to an outer container that holds the specimen container or containers during transport from the collection site to the laboratory. Alternatively, the tracking label 145 may be affixed to a manifest describing the shipment that includes the specimen containers. A rectangular tracking label 145 such as depicted may also secure certain kinds of containers, such as, e.g., by holding closed the hinged lid of a container made of a rigid material.

The above description of the contents and layout of the blank form 100, its division into portions, the subdivision of any portion into sections or otherwise, and the data items thereon is purely illustrative of one particular embodiment of the invention. In any particular embodiment, the location and contents of any words, marks, and/or data items may vary from the depiction in FIG. 1A.

In an embodiment of the invention, the data used to populate the blank form 100 may be viewed, edited, and/or stored electronically. Such electronic manipulation of data is most commonly achieved using one or more computer programs, typically a special-purpose application or applications. In connection with an alternative embodiment of the invention, commercially-available, general-purpose software, e.g., Microsoft Word®, Adobe Acrobat® or Adobe Acrobat Reader®, may be used for some or all data processing associated with the blank form 100. According to an embodiment of the invention, the data is entered using a computer, which may be referred to as a "client" or "workstation," and then the form is printed on a blank form 100.

Electronically recorded data may be stored locally and/or transmitted to a remote computer, which may be referred to as a "server," via a communications infrastructure. The communications infrastructure may comprise any type of public or private network, such as the Internet, an intranet, a virtual private network, or any other link that supports electronic communication from the client to the server. Such communication may be secured, e.g., by encryption and or other well-known means.

Any such electronically recorded data may be used to render and/or reconstruct an image of the chain of custody form at the point of collection and/or to cause the chain of custody form to be printed, e.g., upon a form blank 100. This data may also be shared with other laboratory information systems, e.g., to "pre-accession" the specimen in the laboratory or other computer systems. Pre-accessioning may speed order entry and reduce the opportunities for error that may attend fully manual entry of orders.

In connection with an alternative embodiment of the invention, the content and placement of data may be determined other than at the time the blank form is manufactured. FIG. 1B depicts a blank form 180 in such an embodiment of the invention. The physical structure of the blank form 180 may resemble that of the blank form 100 depicted in FIG. 1A, but this blank form 180 omits the data fields discussed above in connection with FIG. 1A. This omission adds flexibility to the use of the blank form 180. Thus, in connection with an embodiment of the invention comprising this blank form 180, the end-user and/or end-user application software may determine the specific data to be gathered and displayed. In an embodiment of the invention, this determination may depend on, e.g., the nature and/or circumstances of, e.g., the particular specimen, donor, and/or test potentially allowing the content and layout to vary from one form to the next.

FIG. 1B further depicts multiple placements of the form control code 181 on the blank form 180. Despite the omission of data fields on the blank form 180, the form control code is preferably applied to the blank form 180 at the time of manufacture. As depicted in FIG. 1B, the form control code appears in both machine-readable form 182 (e.g., as a bar code) and human-readable form 183.

In another embodiment of the invention, chain of custody may be maintained partly or completely in electronic form, using digital signatures to eliminate some or all handwritten signatures. In this connection, the term "digital signature" may comprise any electronic confirmation of the identity of the nominal signer that may not easily be duplicated without the signer's presence and participation.

For example, obtaining a digital signature may comprise obtaining identifying data via a signer-specific token. This token may be obtained through a public key infrastructure such as is well known in the art, which may comprise, e.g., a so-called smart card or other physical token. Alternatively, the token may be biometric, such as, e.g., a fingerprint, retina scan, or facial geometry, among other possibilities known in the art. For another alternative, the token may be a digital image of a handwritten signature, obtained e.g., by having the signer use a stylus on a sensing device or by placing a paper form on a sensing device, upon which the signature is made with a pen.

Once captured, the identifying token may be included with other data related to the test in a data set that a cryptographic hash function, such as is well known in the relevant art, uses to create a specimen or transaction identifier. In connection with an embodiment of the invention, a digital signature obtained from a donor may be so used to generate a hash value (not pictured) that is printed on one or more portions of the form in human-readable and/or machine-readable form. In connection with a further embodiment of the invention, the specimen or transaction identifier may be printed on one or more seals and/or tracking labels that are to be applied to a specimen container, and the chain of custody may otherwise be fully electronic.

In connection with a fully electronic chain of custody, the computed specimen or transaction identifier may be stored persistently, e.g., in a database management system.

Figure 2:
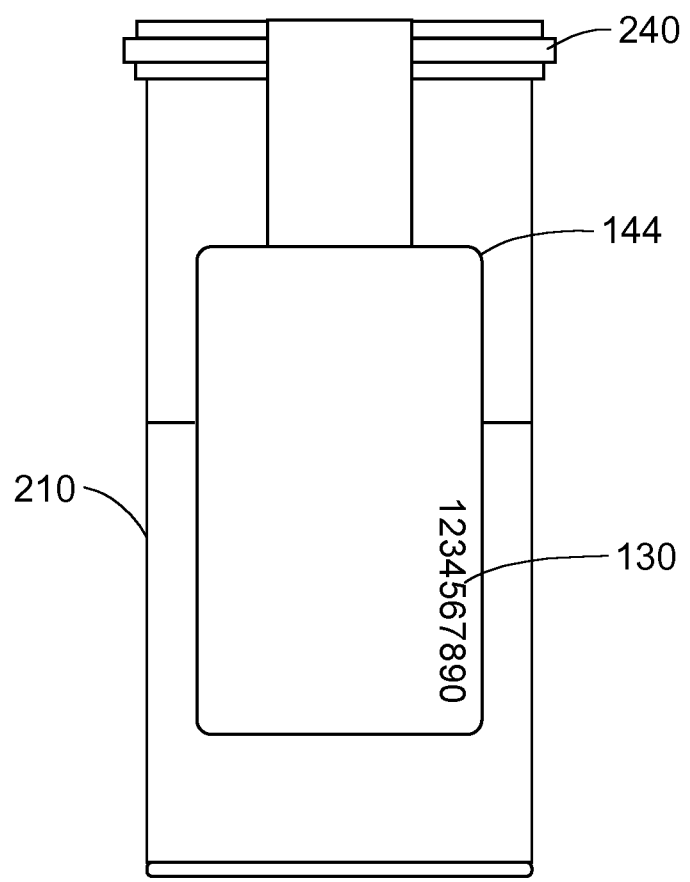
FIG. 2 presents a plan view of a container that is sealed with a security seal according to an embodiment of the invention.

FIG. 2 presents a plan view of a specimen container 210 sealed with a security seal 144 according to an embodiment of the invention. The elongated seal includes the unique identifier 130 that also appears on the data portion 120 (FIG. 1A) of the blank form 100 (FIG. 1A). As depicted in FIG. 2, the specimen container 210 is covered with a removable container lid 240. An elongated seal 144 adheres to the specimen container 210 such that the center portion of the seal 144 is aligned with the center of the lid 240. The section of the seal 144 containing the unique identifier 130 extends past the edge of the lid 240 and adheres to the outside surface of the container 210.

The seal 144 that appears in FIG. 2 is made of a material that is highly destructible in that it that tears very easily, and the seal 144 may therefore be referred to as a "destructible seal." Because the destructible seal 144 adheres to both the container 210 and the lid 240, any attempt to remove the lid 240 is very likely to break the seal 144. Moreover, the fragility of the seal 144 means that attempts to remove the seal 144 intact are very likely to fail and, if persisted in, to destroy the seal 144.

In addition to or as an alternative to destructible seals, other types of seals may be employed to prevent tampering or to deter it by leaving evidence. For example, tamper-evident seals are known in the art that leave behind a message (e.g., "VOID" or "OPENED") on the surface of the container if the seal is removed. Replacement of such a seal, even if possible, does not obliterate the indication that tampering occurred.

Figure 3:
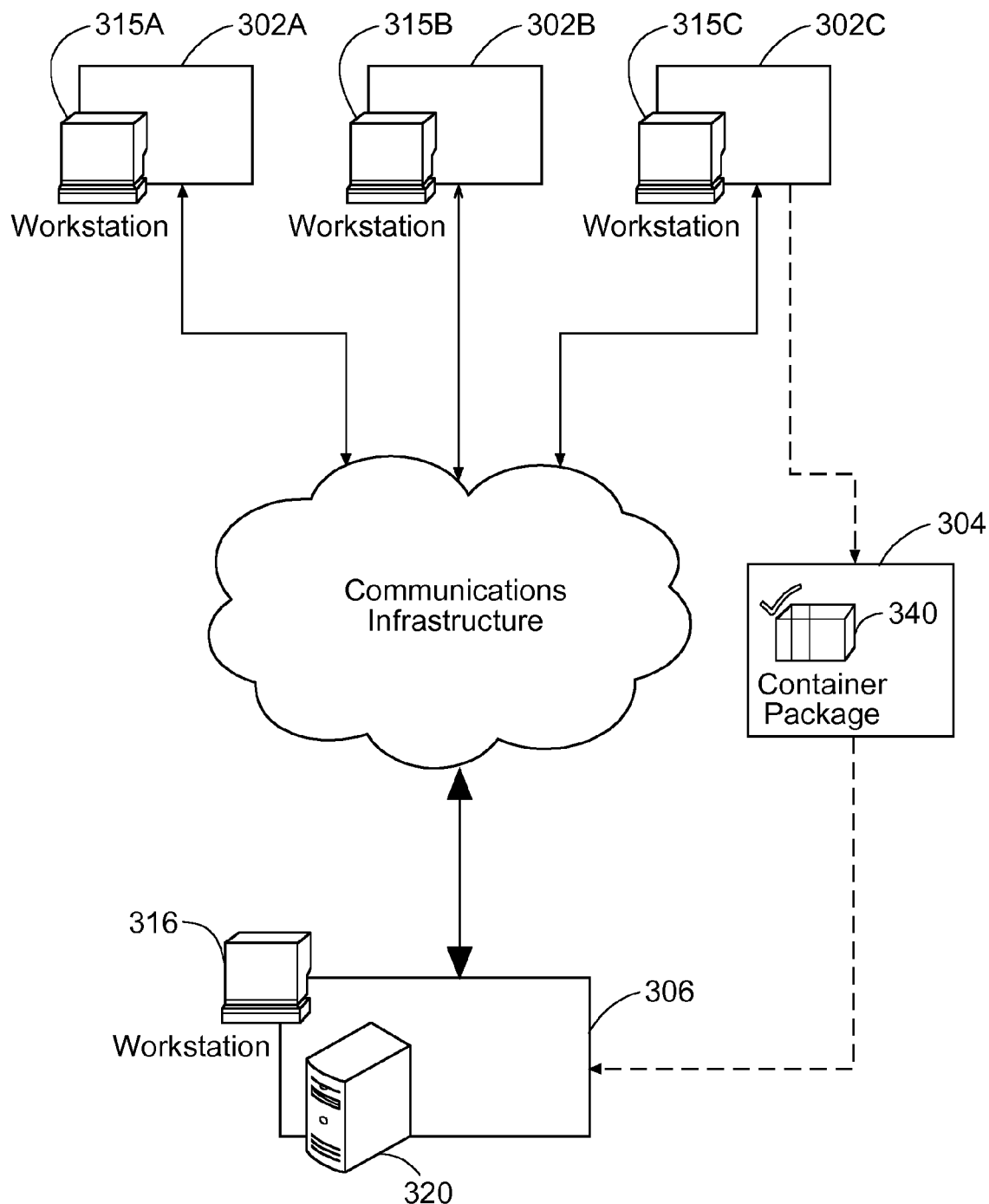
FIG. 3 depicts the entities involved in identifying a sample and documenting its handling from collection to receipt of the sample by the laboratory according to an embodiment of the invention.

FIG. 3 illustrates infrastructure for maintaining a specimen's chain of custody from collection point to laboratory according to an embodiment of the invention. The figure shows the main participants in maintaining a chain of custody from the time of collection to the time of receipt by the laboratory. One skilled in the art will recognize that the specimen handling procedures and the roles of the personnel discussed in conjunction therewith may vary substantially from those described herein without interfering with or changing the principle of operation of the invention.

As depicted in FIG. 3, the principal entities include a collection site 302, a laboratory 306, and a delivery service 304. The term "collection site" 302 may refer to a facility where specimens are collected from a donor for subsequent delivery to a laboratory for analyses. The collector instructs and assists a donor at a collection site 302 and receives and makes an initial inspection of the specimen.

The collection site 302 may keep supplies on hand, e.g., of specimen containers, chemicals for sample preservation, and chain-of-custody sealing tape or seals and forms (pre-printed forms or computer generated), as well as a refrigerator and a computer 315.

The computer 315 may further comprise a central processing unit (CPU) and various forms and configurations of random access and nonvolatile memory. The computer 315 may comprise fixed and/or removable media capable of storing data and/or instructions executable by a CPU. The computer 315 may include a network card through which it connects to a local server which, in turn, is connected to a remote server 320 via a communication infrastructure comprising, e.g., a dedicated wide-area network, the Internet, and/or any other network or link capable of data transmission. The computer 315 may be operable to collect the chain-of-custody form data and to store it locally and/or to transmit it to a server 320, which may be the remote server 320 or another local or remote server. On receiving the data, the server may store it in a database management system, such as is well known in the art.

Alternatively, a mobile collection site 302 may be used to collect samples, particularly from donors who cannot travel to a permanent collection site 302. A mobile collection site 302 may include each of the items found in a permanent collection site 302 described above.

A laboratory 306 may be any facility capable of analyzing biological samples. The laboratory 306 will typically contract with a delivery service 304 to pick up the samples from the collection site 302 and deliver them to the laboratory 306 for analysis. Samples, along with the corresponding chain-of-custody forms, may be hand carried by a delivery service 304 or shipped, e.g., via an express service, such as FedEx, DHL, UPS Priority Service, or a courier, ensuring that specimens arrive at the laboratory no later than the next day.

Once the sample is delivered to the laboratory 306, laboratory personnel inspect the chain-of-custody forms to ensure the accuracy and completeness of the information, and may assign an accession number (a sequential identification number used for tracking purposes at the laboratory) to the sample if necessary. If the apparent condition of the specimen indicates that it has been collected, sealed, or otherwise handled to make it unsuitable or unreliable as a test sample, the laboratory 306 will not test the specimen. An acceptable specimen will be delivered to the appropriate clinical accession area (e.g. urinalysis, chemistry, microbiology) for analysis.

In connection with one exemplary embodiment of the invention, the laboratory 306 maintains all tangible and/or electronic chain-of-custody records.

Figure 4:
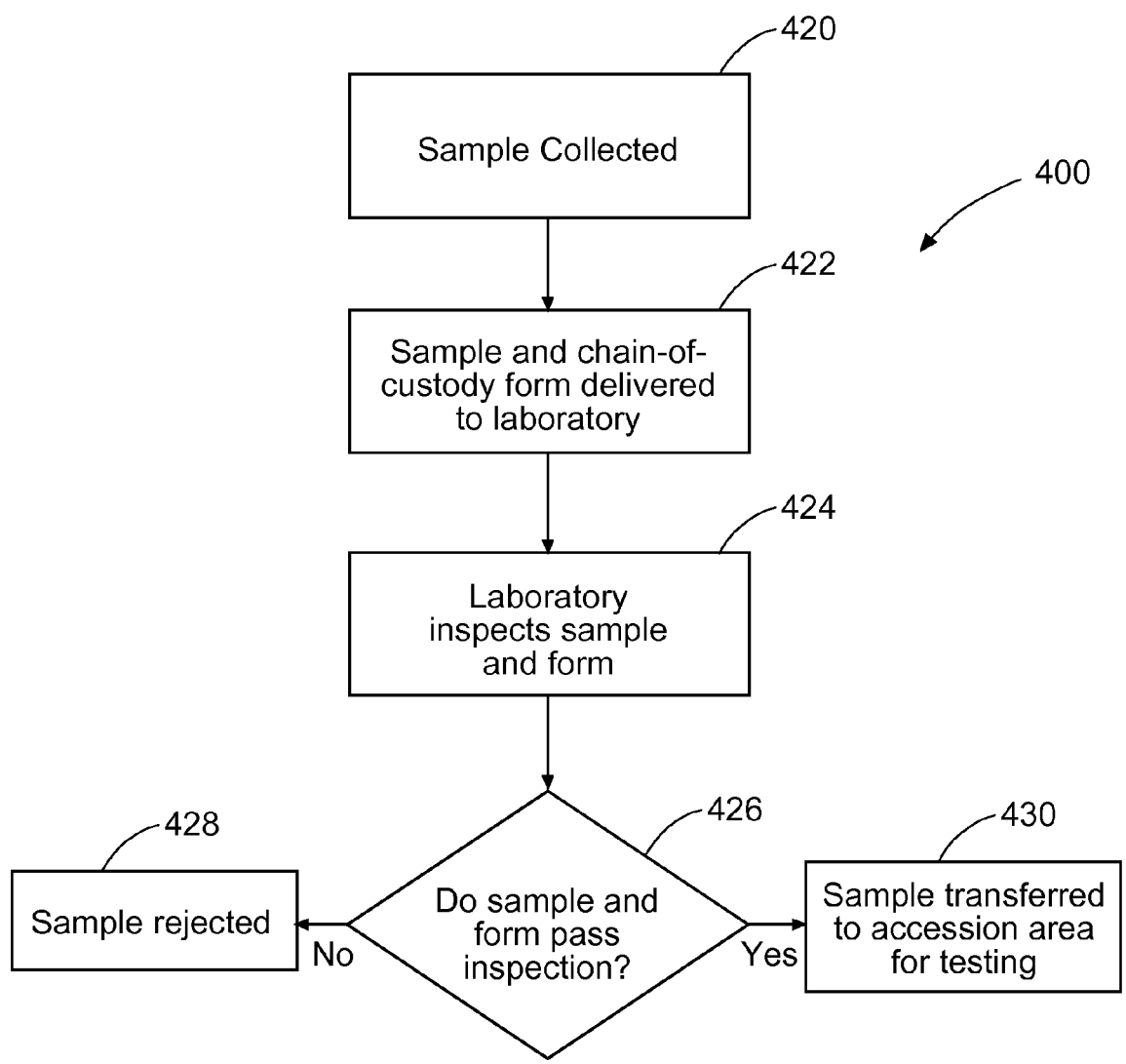
FIG. 4 depicts collection and handling of a sample as may take place in connection with embodiments of the invention.

The flowchart 400 in FIG. 4 depicts sample collection and handling, from the time of collection until delivery to the laboratory, in accordance with an embodiment of the invention. The process begins in block 420 with collection of a sample. Sample collection is discussed in more detail below in connection with FIGS. 5 and 6.

Once a sample has been collected and packed for transport with its associated chain of custody form, a delivery service company 304 (FIG. 3) picks up the samples for transport to the testing laboratory in block 422 (FIG. 4). In an embodiment of the invention, the collector may arrange for the sample to be picked up, e.g., by calling the delivery service company. Alternatively, a standing arrangement may provide for a courier to stop at the laboratory regularly, e.g., every business day, to pick up any samples that may have been collected.

Upon receipt of a sample, the accessioner may in connection with an embodiment of the invention sign and date the chain of custody form and then inspect the received sample in block 424. In embodiments of the invention, this inspection 424 may comprise, e.g., verifying that the samples match the description from the test requisition, reviewing the chain of custody recorded prior to delivery, and/or inspecting the condition of the seal or seals and recording the condition of the seal or seals in a designated space in the chain of custody form. Consequently, in block 426, the accessioner determines whether the sample and chain of custody are acceptable. If any discrepancy and/or error is found (e.g., the collector did not sign the chain of custody, the collector did not check one of the specimen temperature boxes), the sample may be rejected in block 428, although it may in some circumstances be possible to resolve the discrepancy and process the sample. If the accessioner or other laboratory representative determines that the sample and form are both acceptable, the sample, and, in connection with some embodiments of the invention, the chain of custody form will be delivered to the appropriate accession area at step 430 for testing.

The flowchart 430 in FIG. 5 depicts collection 420 of a specimen in connection with an embodiment of the invention. The procedure depicted in this flowchart 430 may be followed, e.g., when a computer, computer terminal, and/or other device for data entry and a printer are present in or conveniently accessible from the area in which the specimen is collected.

Collection begins at step 450 when the donor reaches the collection site. At step 452, data regarding the donor, the requisition, and/or the test may be recorded, e.g., by entry into a computer and/or retrieved, e.g., from one or more local and/or remote databases. The donor is then asked to provide the sample in step 454. To ensure that the sample comprises material from the donor and only material from the donor, the donor may, according to an embodiment of the invention, be accompanied and/or supervised in this step. In connection with embodiments of the invention, provision of the specimen in this step may include allowance for modesty, e.g., when the donor is providing a urine specimen, but such allowance preferably does not preclude supervision that is sufficient to maintain the integrity of the sample.

In any particular instance, a specimen may not be provided following step 454. For example, a donor may decide not to follow through with the test. Or, in some case, a donor may be unable to emit urine for a time consequent to having recently voided. Step 456 represents recognition that a specimen has or has not been provided.

If no specimen has been obtained, the collector receives instructions, e.g., from a manual of procedures or computerized system, in step 458. The instructions may vary depending on the embodiment of the invention, the policies of the collection site, and or the laboratory service provider. In accordance with an embodiment of the invention, for example, the collector may be instructed to explain to an uncooperative donor the reason for the test and the possible consequences of refusal. As another example, the collector may be instructed to allow a donor to wait before attempting again to produce a urine sample. In connection with embodiments of the invention, other instructions may be provided that are appropriate for various other situations.

Following receipt of the instructions, the collector in step 460 records the status of the collection attempt, e.g., by entering data in the provided computer. In step 462, the collector determines, possibly by following the instructions provided in step 458, whether to resume collection. If it is decided not to resume collection, this fact is recorded in step 464, and step 466 represents termination of this collection attempt.

Once the donor has provided a specimen, the collector may, in connection with an embodiment of the invention, verify that the lid is secure and inspects the specimen for possible adulteration. If this inspection reveals that the donor has adulterated the specimen or substituted another specimen for the one requested, a second sample is collected. This inspection may comprise, e.g., measurement of the specimen's temperature promptly after collection If the temperature is unacceptable, possibly indicating, e.g., that the sample was not recently produced by the donor, a second specimen may be collected.

If the temperature of the specimen is acceptable and no evidence of adulteration is found, the collector may proceed to step 470, which may in connection with an embodiment of the invention comprise, e.g., recording the type and temperature of the specimen. Step 470 may comprise recording any remarks that the collector wishes to add regarding the specimen or its collection. In connection with embodiments of the invention, recording information in step 470 may comprise, e.g., handwriting, typing, and or stamping information on the blank form and/or entering information for electronic storage and/or printing on a blank form. In an embodiment of the invention, entry of the test information into, e.g., a computer, is followed in step 472 by printing a chain-of-custody form upon a blank form.

In an embodiment of the invention, step 474 comprises the collector affixing a tamper-evident seal from a form across the container lid in the presence of the donor, dating the seal before or after it has been placed on the specimen container, and having the donor initial the seal. As shown in FIG. 2, the seal is one continuous adhesive strip that is placed over the top of the specimen lid and then adheres to the specimen container on both sides. If, while sealing and initialing a seal, the collector or donor accidentally breaks or damages the seal, the collector must apply a second seal if the form was printed from a blank form 100 (FIG. 1A) that included more seals than needed, or print another form with a different form control code.

Returning to FIG. 5, at step 476, the collector, in the presence of the donor, signs and dates the certification statement included in the chain-of-custody section 138 (FIG. 1A) of the data portion (FIG. 1A) 120 while the donor is present. In connection with an embodiment of the invention, the collector also notes the time and date of collection and the identity of the delivery service 304 (FIG. 3) that is conveying the specimen to the laboratory. Also in step 476, the collector instructs the donor to read and then sign the certification statement. After the donor signs and dates the certification statement and provides the other requested information, the donor may be excused. The donor receipt 130 (FIG. 1A) may be removed from the form and given to the donor before he or she leaves the collection site.

In connection with an embodiment of the invention, the collector in step 478 scans the bar code from the chain-of-custody form, the seal or seals, and/or a tracking label. The collector may place the specimen container or containers in one or more specimen bags, which may then be sealed. In connection with an embodiment of the invention, a tracking label bearing the form identification code in human-readable and/or machine-readable form may separated from the chain-of-custody form and applied to the specimen bag.

In connection with an embodiment of the invention, the portion of the chain-of-custody form from which the seal or seals and/or the tracking label may be removed may, following removal of the seal or seals and/or tracking label, be separated from the remainder of the chain-of-custody form and discarded.

Step 480 represents electronic transmission of information related to the donor, test, collection, and/or specimen to a lab information system in connection with an embodiment of the invention.

The flowchart 500 in FIG. 6 depicts collection of a specimen in connection with an embodiment of the invention. The procedure depicted in this flowchart 500 may be followed, e.g., when a computer, computer terminal, and/or other device for data entry and a printer are not present in or conveniently accessible from the area in which the specimen is collected.

In steps 510, 512, and 514, the donor presents at the collection site, data is gathered, and the donor is escorted to provide a sample in much the same was as is described above in connection with FIG. 5. In step 516, in connection with an embodiment of the invention, the chain-of-custody form is printed while the donor provides the sample. Correspondingly, in connection with an embodiment of the invention, if collection 500 terminates without provision of a specimen, the printed chain-of-custody form is destroyed in step 538.

The invention thus has been disclosed broadly and illustrated in reference to representative embodiments described above. Those skilled in the art will recognize that various modifications can be made to the present invention without departing from the spirit and scope thereof.

We claim:

1. A method of maintaining a chain of custody, comprising:

causing a printer to print demographic information and test information upon a form that consists of a single printable sheet that is not affixed to any other sheets, the single printable sheet consisting of only a single ply that is not affixed to any other plies, the sheet comprising
- at least a first portion and a second portion,
- one or more seals within the second portion, each seal being removable from the sheet and capable of being affixed to a closed container so that contents of the container cannot be tampered with without either removing the seal or causing visible damage to the seal, and
- an identifier that is unique to the form and is recorded at least once within the first portion and at least once upon each of the one or more seals in the second portion;

collecting from a donor at least one specimen comprising biological material, the collecting taking place under supervision of an administrator;

placing the biological material comprised by one of the specimens into a container; and closing the container and affixing at least one of the one or more seals to the container so that contents of the container cannot be tampered with without either removing the seal or causing visible damage to the seal.

2. The method of claim 1, comprising performing at least one assay upon the specimen.

3. The method of claim 1, comprising acquiring a signature of the administrator.

4. The method of claim 1, comprising acquiring a signature of the donor.

5. The method of claim 3 or claim 4, wherein the acquired signature is a digital signature.

6. The method of claim 5, comprising recording a representation of the digital signature upon the form.

7. The method of claim 1, wherein the identifier comprises a form control code that is unique to the printable sheet.

8. The method of claim 7, wherein the identifier is present in human-readable form.

9. The method of claim 7, wherein the identifier is present in machine-readable form.

10. The method of claim 1, wherein the first portion of the printable sheet comprises:
- a first section within the first portion, comprising one or more marked spaces for recording demographic information and test information and one or more indicia of respective purposes of the one or more marked spaces; and
- a second section within the first portion, comprising a marked signature space for the donor to affix a signature and one or more indicia of a purpose of the marked signature space.

11. The method of claim 1, wherein the printable sheet comprises a perforation for separating the second portion from the first portion.

12. The method of claim 1, wherein the printable sheet comprises a third portion, and the identifier is recorded at least once within the third portion.

13. The method of claim 12, wherein the printable sheet comprises:
- a perforation for separating the first portion from the second portion or from the third portion; and
- a perforation for separating the second portion from the first portion or from the third portion.

14. The method of claim 1, wherein:
- the printable sheet lacks a marked space for recording demographic information;
- the printable sheet lacks a marked space for recording test information; and
- causing the printer to print the form comprises causing the printer to print demographic information and test information upon the printable sheet.

15. The method of claim 1, wherein the form bears the unique identifier in at least one place before the printer has printed anything upon the form.

* * * * *